US007338775B1

(12) United States Patent
Ostanin et al.

(10) Patent No.: US 7,338,775 B1
(45) Date of Patent: Mar. 4, 2008

(54) ENZYME ASSAY AND USE THEREOF

(75) Inventors: Kirill Ostanin, Salt Lake City, UT (US); Thomas Hunsaker, Concord, CA (US)

(73) Assignee: Myriad Genetics, Inc., Salt Lake City, UT (US)

( * ) Notice: Subject to any disclaimer, the term of this patent is extended or adjusted under 35 U.S.C. 154(b) by 0 days.

(21) Appl. No.: 11/351,899

(22) Filed: Feb. 9, 2006

Related U.S. Application Data

(60) Provisional application No. 60/651,824, filed on Feb. 9, 2005.

(51) Int. Cl.
*C12Q 1/50* (2006.01)
(52) U.S. Cl. ...................................................... 435/17
(58) Field of Classification Search ................. None
See application file for complete search history.

(56) References Cited

U.S. PATENT DOCUMENTS

| | | | |
|---|---|---|---|
| 4,235,961 A | 11/1980 | Lundin | |
| 4,923,796 A | 5/1990 | Deneke et al. | |
| 5,124,141 A | 6/1992 | Makler | |
| 5,286,627 A | 2/1994 | Ueda et al. | |
| 5,698,685 A | 12/1997 | Summerton et al. | |
| 5,750,344 A | 5/1998 | Doyle | |
| 5,766,963 A | 6/1998 | Baldwin et al. | |
| 5,780,256 A | 7/1998 | Ueda et al. | |
| 5,792,821 A | 8/1998 | Bowen | |
| 5,798,214 A | 8/1998 | Squirrell | |
| 5,834,318 A | 11/1998 | Buettner | |
| 5,866,341 A | 2/1999 | Spinella et al. | |
| 5,877,278 A | 3/1999 | Zuckermann et al. | |
| 5,916,761 A | 6/1999 | Koga et al. | |
| 5,962,337 A | 10/1999 | Ohlmeyer | |
| 5,968,787 A | 10/1999 | Iwata et al. | |
| 6,015,561 A | 1/2000 | Alvarez | |
| 6,022,713 A | 2/2000 | Noguchi et al. | |
| 6,093,798 A | 7/2000 | Floyd et al. | |
| 6,107,059 A | 8/2000 | Hart | |
| 6,156,511 A | 12/2000 | Schatz et al. | |
| 6,162,926 A | 12/2000 | Murphy et al. | |
| 6,306,617 B1 | 10/2001 | Gunzer et al. | |
| 6,380,380 B1 | 4/2002 | Kaufman | |
| 6,413,733 B1 | 7/2002 | Nagel et al. | |
| 6,599,711 B2 | 7/2003 | Crouch et al. | |
| 2002/0172991 A1 | 11/2002 | Crouch et al. | |

OTHER PUBLICATIONS

Hillard et al. Talanta 1998;45:507-512.*
Maeda et al. Chem. Pharm. Bull. 2001;49(5):622-625.*
Batchelor et al., "A resorufin-based fluorescent assay for quantifying NADH", *Anal Biochem.*, Jun. 2002, 305(1):118-119.
Bunin et al., "A General and Expedient Method for the Solid-Phase Synthesis of 1,4-Benzodiazepine Derivatives", *J. Am. Chem. Soc.*, 1992, 114:10997-10998.
Devlin et al., "Random peptide libraries: a source of specific protein binding molecules", *Science*, Jul. 1990, 249:404-406.
Gallop et al., "Applications of combinatorial technologies to drug discovery. 1. Background and peptide combinatorial libraries", *Journal of Medicinal Chemistry*, Apr. 29, 1994, 37(9):1233-1251.
Gold, "Oligonucleotides as Research, Diagnostic, and Therapeutic Agents", *The Journal of Biological Chemistry*, Jun. 9, 1995, 270(23):13581-13584.
Gordon et al., "Applications of Combinatorial Technologies to Drug Discovery. 2. Combinatorial Organic Synthesis, Library Screening Strategies, and Future Directions", Journal of Medicinal Chemistry, May 13, 1994, 37(10):1385-1401.
Graves et al., "Protein phosphorylation and signal transduction", *Pharmacol. Ther.*, May-Jun. 1999, 82(2-3):111-121.
Kao et al., "Engineered biosynthesis of a complete macrolactone in a heterologous host", *Science*, Jul. 1994, 265:509-512.
Koga et al., "Biochemical Characterization, Cloning, and Sequencing of ADP-Dependent (AMP-Forming) Glucokinase from Two Hyperthermophilic Archaea, *Pyrococcus furiosus* and *Thermococcus litoralis*1", *J. Biochem.*, 2000, 128:1079-1085.
Kengen et al., "Purification and Characterization of a Novel ADP-dependent Glucokinase from the Hyperthermophilic Archaeon *Pyrococcus furiosus*", *The Journal of Biological Chemistry*, Dec. 22, 1995, 270(51):30453-30457.
Lei et al., "Mechanism of Reduced Flavin Transfer from *Vibrio harveyi* NADPH-FMN Oxidoreductase to Luciferase", *Biochemistry*, 1998, 37:14623-14629.
McDaniel et al., "Engineered biosynthesis of novel polyketides", *Science*, Dec. 3, 1993, 262:1546-1550.
Moran et al., "Radio Frequency Tag Encoded Combinatorial Library Method for the Discovery of Tripeptide-Substituted Cinnamic Acid Inhibitors of the Protein Tyrosine Phosphatase PTP1B", *J. Am. Chem.*, 1995, 117:10787-10788.
Sakuraba et al., "ADP-dependent Glucokinase/Phosphofructokinase, a Novel Bifunctional Enzyme from the Hperthermophilic Archaeon *Methanococcus jannaschii*", *The Journal of Biological Chemistry*, Apr. 22, 2002, 277(15):12495-12498.
Schenk et al., "Signal perception and transduction: the role of protein kinases", *Biochim Biophys Acta.*, Feb. 4, 1999, 1449(1):1-24.
Scott et al., "Searching for peptide ligands with an epitope library", *Science*, Jul. 27, 1990, 249:386-390.
Simon et al., "Peptoids: A modular approach to drug discovery", *Proc. Natl. Sci.*, Oct. 1992, 89:9367-9371.
Srinivasan et al., "ADP-Specific Sensors Enable Universal Assay of Protein Kinase Activity". *Chemistry & Biology*, Apr. 2004, 11:449-508.
Stachelhaus et al., "Rational design of peptide antibiotics by targeted replacement of bacterial and fungal domains", *Science*, Jul. 7, 1995, 269:69-72.
Thelen et al., "Molecular Cloning and Expression Analysis of the Mitochondrial Pyruvate Dehydrogenase from Maize1", *Plant Physiology*, Feb. 1999, 119:635-643.

(Continued)

Primary Examiner—Ralph Gitomer
Assistant Examiner—Bin Shen
(74) Attorney, Agent, or Firm—Andrew Gibbs; Jay Z. Zhang; Myriad IP Department

(57) ABSTRACT

An assay and kit for determining the activity of an enzyme such as kinase, ATPase and GTPase is disclosed. The assay and kit are useful in drug screening to select modulators of such an enzyme.

7 Claims, 6 Drawing Sheets

OTHER PUBLICATIONS

Tuininga et al., "Molecular and Biochemical Characterization of the ADP-dependent Phosphofructokinase from the Hyperthermophilic Archaeon *Pyrococcus furiosus*", *The Journal of Biological Chemistry*, Jul. 23, 1999, 274(30):21023-21028.

Tornheim et al., "Specific Enzymatic Spectrophotometric Assay of Adenosine 5'- Diphosphate", *Analytical Biochemistry*, 1993, 211:329-330.

Verhees et al., "Biochemical adaptations of two sugar kinases from the hyperthermophilic archaeon *Pyrococcus furiosus*", *Biochem. J.*, 2002, 366:121-127.

"ADP Hunter Assay 90-0077, Fluorescence Intensity Detection", *DiscoverRx*, Product Information Sheet, Aug. 16, 2005, pp. 1-6.

"Kinase-Glo Luminescent Kinase Assay", *Promega*, Product Information Sheet, Dec. 2002, pp. 1-12.

TK Substrate Quest Kit, Fluorescence Intensity Detection, Product code 90-0072, *DiscoverRx*, Product Information Sheet, Aug. 2005, pp. 1-6.

"Vybrant Cytotoxicity Assay Kit (V-23111)", *Molecular Probes*, Product Information Sheet, Jul. 2002, pp. 1-3.

* cited by examiner

ENZYME ASSAY AND USE THEREOF

CROSS-REFERENCE TO RELATED U.S. APPLICATION

This application claims priority to U.S. Provisional Patent Application Ser. No. 60/651,824 filed Feb. 9, 2005, the content of which is incorporated herein by reference in its entirety.

FIELD OF THE INVENTION

The present invention generally relates to biochemical assays, and particularly to the detection of the activity of enzymes, such as kinases, and use thereof.

BACKGROUND OF THE INVENTION

With at least 510 members, human protein kinases constitute the largest family of potential drug targets that have drawn tremendous attention from both academic and industrial researchers due to the demonstrated key regulatory roles of protein phosphorylation in essentially all cellular processes. Graves & Krebs, *Pharmacol. Ther.* 82:111 (1999); Schenk & Snaar-Jagalska, *Biochim. Biophys. Acta.*, 1449:1 (1999). It is estimated that approximately 30% of current research spending on drug development focuses on this enzyme family, particularly in the areas of cancer, diabetes and immune diseases. Several kinase inhibitors have been approved by the FDA as anti-cancer drugs (Herceptin®, Gleevec®, and Tarceva®), and at least thirty modulators of protein kinase activities are currently being tested in late stage clinical trials. In addition, inhibitors of a number of kinases that act on non-protein substrates are also being developed as drug candidates. Such kinases include, e.g., phosphatidylinositol-3-kinase, ceramide kinase, glucokinase, guanylate kinase, adenosine kinase, and polyphosphate kinase. Efforts in drug screening to identify additional kinase inhibitors are still continuing.

Because there are many validated kinase targets, it is desirable to have a universal kinase assay available that can be applied to a large number of, if not all, kinases. In this regard, the commercially available assays from Promega and Cambrex that are based on monitoring ATP-to-ADP conversion in the course of enzymatic phosphorylation are potentially applicable to all ATP-dependent kinases. However, a serious drawback of this approach is that it relies on the determination of substrate disappearance rather than product accumulation and, hence, is not suitable for the quantification of the initial rate of the enzymatic reactions (the most informative and reliable measure of enzyme activity) with high signal-to-background ratio.

Recently, two novel homogeneous assays for ADP that employ an ADP-specific aptamer or ADP-dependent ribozyme as detection reagents have been developed and their utility for measuring activity of protein kinases has been demonstrated. Srinivasan et al., *Chem. Biol.*, 11:499 (2004). However, the signal-to-background ratio observed in such assays are very low, and as such, the general applicability of these techniques remains to be further tested. In addition, the assays also have the drawback of requiring radioactively labeled ATP and thus are associated with radioactive hazardous waste.

As interest in kinase-based drug development continues intensifying unabatedly, there is great need for highly sensitive and easy to use assays that can be applied to a broad range of kinases.

BRIEF SUMMARY OF THE INVENTION

The present invention provides a method for measuring the enzymatic activity of an enzyme that catalyzes a biochemical reaction producing ADP or GDP. The method has a high sensitivity, is convenient to use and amenable to high throughput screening. In addition, it is applicable to almost all ATPases, GTPases, and kinases that utilize ATP or GTP.

In one embodiment, the biochemical reaction involves converting ATP to ADP. For example, the method of the present invention can be used to measure the activity of any ADP-generating enzymes including, but not limited kinases and ATPases. In another embodiment, the biochemical reaction involves the conversion from GTP to GDP, and the method is used to measure the activity of any GDP-generating enzymes including, but not limited to, GTPases and GTP-dependent kinases.

In another aspect, the present invention also provides a method of selecting modulators (inhibitors or activators) of an enzyme that catalyzes a biochemical reaction producing ADP or GDP. The modulators can directly modulate the activity of the enzyme, or modulate the activity of the enzyme indirectly by, e.g., modulating the amount of the enzyme. In a preferred embodiment, the method is used to select inhibitors of the activity of an enzyme that catalyzes a biochemical reaction producing ADP or GDP. Thus, for example, the method can be used in primary or secondary drug screening assays for inhibitors of the activities of kinases, ATPases, and GTPases.

In yet another aspect of the present invention, a kit is provided, which includes (1) a reaction buffer comprising ATP, and optionally a kinase and/or a suitable substrate of the kinase, (2) a detection mixture comprising glucose, NADP, glucose-6-phosphate dehydrogenase, diaphorase, and resazurin, and (3) an ADP-dependent hexokinase (e.g., glucokinase). Preferably, the kit should contain, in a carrier or compartmentalized container, the above reagents. The carrier can be a container or support, in the form of, e.g., bag, box, tube, vial, rack, and is optionally compartmentalized. The carrier may define an enclosed confinement for safety purposes during shipment and storage.

Other features and advantages of the invention will be apparent from the following detailed description and drawings, and from the claims.

DETAILED DESCRIPTION OF THE INVENTION

Figure 1:
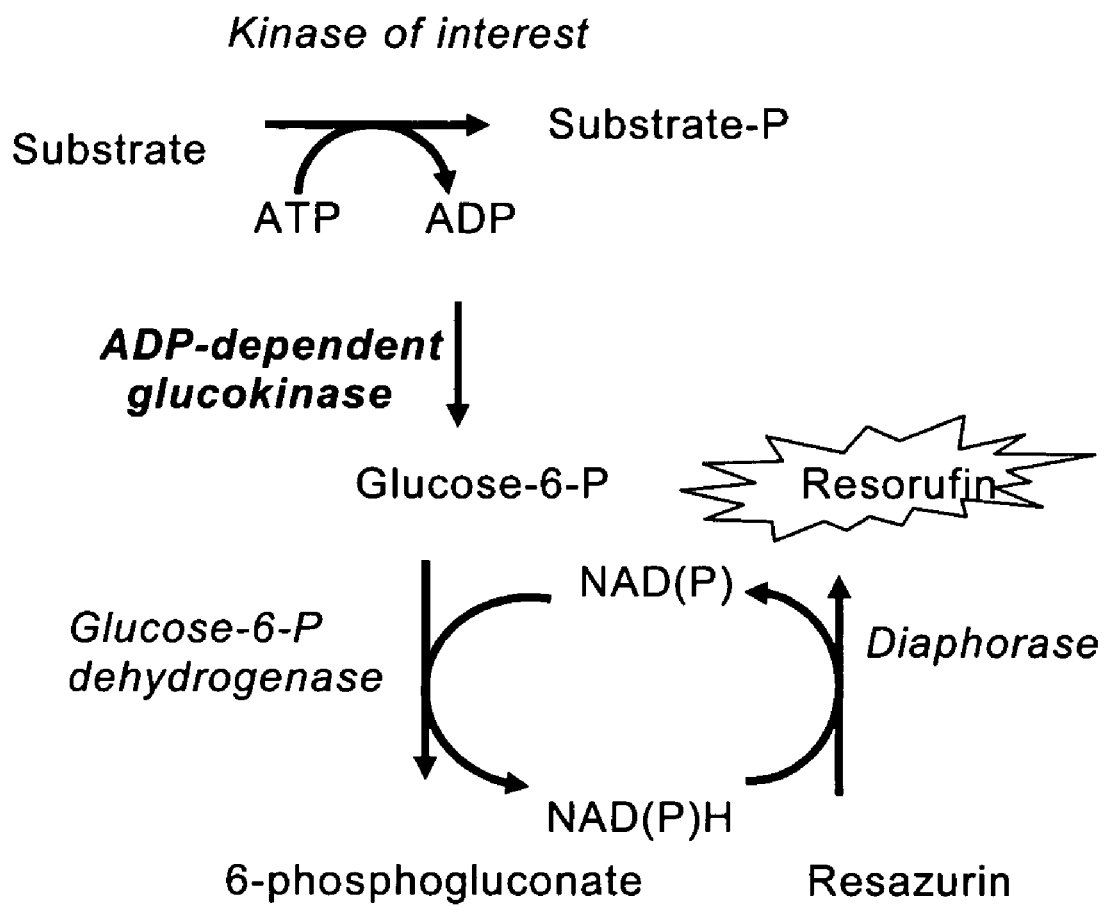
FIG. 1 is a general scheme of an embodiment of the assay of the present invention.

The present invention provides an assay for the enzymatic activity of an enzyme that catalyzes a biochemical reaction producing ADP or GDP. The assay generally includes the steps of: (a) contacting a substrate with ATP or GTP in the presence of said enzyme under conditions that would normally allow at least a portion of said ATP or GTP to be converted to ADP or GDP, respectively; (b) reacting the ADP or GDP with a phosphoryl group acceptor which is a hexose or hexose derivative such as hexose phosphate, in the presence of an ADP- or GDP-dependent hexokinase, a dehydrogenase, NAD(P) or an analog thereof, and a dye in an oxidized state, under conditions such that the dye in an oxidized state is converted to a reduced state with fluorescence emission; and (c) determining the activity of the enzyme based on the fluorescence emitted by the dye in the reduced state. Preferably, the dye is resazurin, and the dye in reduced state is resorufin. Also preferably, the reacting step is conducted in the presence of a divalent cation (e.g., $Mg^{2+}$, $Co^{2+}$, $Ca^{2+}$, $Zn^{2+}$, $Mn^{2+}$), and preferably at a concentration of at least 1 mM, more preferably at least 5 mM, and most preferably at 10 mM.

Specifically, the assay method of the present invention measures the amount ADP or GDP produced by the biochemical reaction catalyzed by the enzyme whose activity is being determined, and couples the ADP or GDP amount to a fluorescent readout generated by a fluorescent dye (e.g., resorufin or a fluorescent analog thereof). This unique combination leads to a very low ADP detection limit and an unusually high signal to background ratio. Typically, the ADP or GDP amount is relatively low at the beginning of a catalytic reaction, and it is the beginning stage of a catalytic reaction that most accurately reflects the enzyme kinetics. Thus, the high signal/background ratio and high sensitivity in the measurement of low ADP or GDP concentrations make the assay of the present invention highly sensitive and reliable. In addition, unlike the vast majority of the currently available methods, the assay of the present invention is universal and is applicable to almost all kinases and other ADP/GDP-generating enzymes.

In one embodiment, the method is used for determining the activity of an ATPase or kinase that catalyzes a biochemical reaction producing ADP, and comprises the steps of: (a) contacting a substrate with ATP in the presence of said ATPase or kinase under conditions that normally would allow at least a portion of said ATP to be converted to ADP; (b) reacting the ADP with a phosphoryl group acceptor which is a hexose or a hexose derivative such as hexose phosphate, in the presence of an ADP-dependent hexokinase, a dehydrogenase, NAD(P) or an analog thereof, resazurin or a salt or analog thereof, under conditions such that fluorescent resorufin is produced; and (c) determining the activity of the ATPase or kinase based on measurement of fluorescence emitted by the resorufin.

In another embodiment, the method is used to determine the activity of a GTPase or kinase that catalyzes a biochemical reaction producing GDP, and includes the steps of: (a) contacting a substrate with GTP in the presence of said GTPase or kinase under conditions that normally would allow at least a portion of said GTP to be converted to GDP; (b) reacting the GDP with D-glucose in the presence of a GDP-dependent hexokinase, glucose-6-P dehydrogenase, NAD(P) or an analog thereof, resazurin or a fluorescent analog thereof, and diaphorase under conditions such that fluorescent resorufin is produced; and (c) determining the activity of the GTPase or kinase based on fluorescence emitted by the resorufin.

Thus, the method of the present invention is applicable to any enzymes that catalyzes a biochemical reaction producing ADP and/or GDP. That is, the method of the present invention is useful in determining the activity of any kinase that utilizes ATP and/or GTP as phosphoryl group donor. Examples of applicable enzymes include, but are not limited to, protein kinases, and kinases specific to non-protein substrates (e.g., phosphatidylinositol-3-kinase, ceramide kinase, glucokinase, guanylate kinase, adenosine kinase and polyphosphate kinase). Other examples of applicable enzymes include ATPases and GTPases.

Accordingly, when the enzyme to be assayed is an ATPase or a kinase that catalyze a biochemical reaction that utilizes ATP and produces ADP, the enzymatic reaction is enabled in the presence of ATP, the enzyme, and a suitable substrate of the enzyme, and under conditions sufficient to allow the enzymatic reaction to occur, thus producing a phosphorylated substrate and ADP. In accordance with the present invention, the enzyme activity is determined based on the amount of ADP produced in the enzymatic reaction.

The amount of the ADP product is determined through a cascade of biochemical reactions. First, the ADP is reacted with a phosphoryl group acceptor which is a hexose or a hexose derivative such as hexose phosphate under the catalysis of an ADP-dependent hexokinase. Examples of suitable phosphoryl group acceptors include, but are not limited to, aldohexoses (e.g., D-allose, D-altrose, D-glucose, D-mannose, D-gulose, D-idose, D-galactose, D-talose), ketohexoses (e.g., D-Fructose, D-Psicose, D-Sorbose and D-Tagatose), D-glucosamine, D-deoxy-D-glucose, D-fructose 6-phosphate, D-fructose 1-phosphate, and D-glucose 6-phosphate.

The ADP-dependent hexokinase can be any suitable enzyme that catalyzes the transfer of a phosphoryl group (e.g., the β-phosphoryl group) of ADP onto the hexose or hexose derivative. The ADP-dependent hexokinase are typically selective with respect to phosphoryl group donar, i.e., the hexokinase is substantially selective for ADP over ATP, with a Km value for ATP is at least 10 times higher than that for ADP. Preferably, the Km value for ATP is at least 100 times, and more preferably at 1000 times higher than that for ADP. Examples of suitable ADP-dependent hexokinases include ADP-dependent glucokinase (see e.g., Kengen et al., *J. Biol. Chem.*, 270:30453-30457 (1995); and Koga et al., *J. Biochem.*, 128:1079-1085 (2000))), ADP-dependent phosphofructokinase (see e.g., Tuining a et al., *J. Biol. Chem.*, 274:21023-21028 (1999)), and ADP-dependent glucokinase/phosphofructokinase from the hyperthermophilic archaeon *methanococcus jannaschii* (see Sakuraba et al., *J. Biol. Chem.*, 277:12495-12498 (2002)).

The phosphorylation product generated through the catalysis by the ADP-dependent hexokinase is then oxidized or dehydrogenated in the presence of a suitable dehydrogenase and nicotinamide adenine dinucleotide or nicotinamide adenine dinucleotide phosphate, i.e., NAD(P) or an analog thereof, thus reducing the NAD(P) or analog thereof to NAD(P)H or an analog thereof. NAD and NADP are well-known enzyme cofactors widely used in the art for the enzyme activity measurements. Any suitable NAD analogs and NADP analogs can also be used so long as they are useful in facilitating oxidation reactions. Suitable NAD analogs and NADP analogs include, e.g., 3-acetylpyridine-NAD, 3-acetylpyridine-NADP, 3-pyridinealdehyde-NAD and 3-pyridinealdehyde-NADP. Other generally known NAD and NADP analogs in the art include those disclosed in, e.g., U.S. Pat. Nos. 5,124,141; 5,286,627; 5,780,256; and 6,380,380; and *The Pyridine Nucleotide Coenzymes*, edited by Everse et al., Academic Press, New York, 1982, all of which are incorporated herein by reference.

The reduced form of NAD(P) or analog thereof, i.e., NAD(P)H or analog thereof is then utilized to facilitate the conversion of a dye from an oxidized state to a reduced state. The dye has an oxidized state and a reduced state, and the reduced state can be distinguished from the oxidized state in that the reduced state is associated with fluorescence emission whereas the oxidized state is substantially free of fluorescence emission. In a preferred embodiment, the dye in oxidized state is resazurin (7-hydroxy-3H-phenoxazin-3-one 10-oxide) or a salt or analog thereof. Resazurin sodium salt is available commercially from Aldrich (catalog no. 19, 930-3). As facilitated by NAD(P)H, resazurin is reduced to the fluorescent resorufin (7-hydroxy-3H-phenoxazin-3-one). It is noted that resorufin is also available commercially from Aldrich (catalog no. 42,445-5). Quantitative or qualitative fluorometric measurement of fluorescent resorufin provides indication of the activity of the enzyme being assayed.

A preferred embodiment of the method of measuring an enzyme activity is illustrated in FIG. 1. In this embodiment, the activity of a kinase of interest in measured. Thus, the method comprises: (1) providing a reaction mixture comprising a kinase of interest, ATP and a substrate of the kinase, wherein ADP is generated as a result of the enzyme activity of the kinase; (2) adding to the reaction mixture an ADP-dependent glucokinase, glucose, NADP, glucose-6-phosphate dehydrogenase, diaphorase, and resazurin, and incubate the resulting mixture under conditions sufficient to convert resazurin to fluorescent resorufin; and (3) detecting resorufin. Specifically, the embodiment illustrated in FIG. 1 exploits a unique ability of the glucokinases found in several species of Archaebacteria to selectively utilize ADP as a donor of phosphoryl group for the phosphorylation of glucose. See Kengen et al., *J. Biol. Chem.*, 270:30453-30457 (1995); Koga et al., *J. Biochem.*, 128:1079-1085 (2000); and Sakuraba et al., *J. Biol. Chem.*, 277:12495-12498 (2002). For instance, it has been shown that glucokinase from *P. furiosus* exhibits at least 300-fold higher catalytic activity in the presence of ADP compared with that measured using ATP as substrate. Thus, ADP released in the course of the reaction catalyzed by the kinase of interest can be selectively converted by ADP-dependent glucokinase to AMP and glucose-6-phosphate even in the presence of high excess of ATP. Formation of glucose-6-phosphate can be monitored using a coupled enzyme assay which employs glucose-6-phosphate dehydrogenase and diaphorase. The latter enzymes generate a readily detectable fluorescent product, resorufin, in the presence of glucose-6-phosphate as well as NADP and resazurin.

In another embodiment of the present invention, the enzyme to be assayed is a GTPase or a kinase that catalyzes a biochemical reaction that utilizes GTP and produces GDP. The enzymatic reaction is enabled in the presence of GTP, the enzyme, and a suitable substrate of the enzyme, and under conditions sufficient to allow the enzymatic reaction to occur, thus producing a phosphorylated substrate and GDP. In accordance with the present invention, the enzyme activity is determined based on the amount of GDP produced in the enzymatic reaction.

The amount of the GDP product is determined through a cascade of coupled biochemical reactions. First, the GDP is reacted with a phosphoryl group acceptor which is a hexose or a hexose derivative such as hexose phosphate under the catalysis of a GDP-dependent hexokinase. Examples of suitable phosphoryl group acceptors include, but are not limited to, aldohexoses (e.g., D-allose, D-altrose, D-glucose, D-mannose, D-gulose, D-idose, D-galactose, D-talose) ketohexoses (e.g., D-Fructose, D-Psicose, D-Sorbose and D-Tagatose), D-glucosamine, D-deoxy-D-glucose, D-fructose 6-phosphate, D-fructose 1-phosphate, D-glucose 6-phosphate.

The GDP-dependent hexokinase can be any suitable enzyme that catalyzes the transfer of a phosphoryl group (e.g., the β-phosphoryl group) of GDP onto the hexose or hexose derivative. The GDP-dependent hexokinase are typically selective with respect to phosphoryl group donar, i.e., the hexokinase is substantially selective for GDP over GTP, with a Km value for GTP is at least 10 times higher than that for GDP. Preferably, the Km value for GTP is at least 100 times, and more preferably at 1000 times higher than that for GDP. Examples of suitable GDP-dependent hexokinases include the ADP-dependent phophofructokinase from *P. furiosus* (see e.g., Tuining a et al., *J. Biol. Chem.*, 274: 21023-21028 (1999)), and ADP-dependent glucokinase/phosphofructokinase from the hyperthermophilic archaeon *methanococcus jannaschii* (see Sakuraba et al., *J. Biol. Chem.*, 277:12495-12498 (2002)).

The phosphorylation product generated through the catalysis by the GDP-dependent hexokinase is then oxidized or dehydrogenated in the presence of a suitable dehydrogenase and nicotinamide adenine dinucleotide or nicotinamide adenine dinucleotide phosphate, i.e., NAD(P) or an analog thereof, thus reducing the NAD(P) or analog thereof to NAD(P)H or an analog thereof. The reduced form of NAD (P) or analog thereof, i.e., NAD(P)H or analog thereof is then utilized to facilitate the conversion of a dye such as resazurin to fluorescent resorufin as described above, and the GTPase or GTP-utilizing kinase activity is determined based on fluorometric measurement of the fluorescent resorufin.

One of the most important applications of the assay method of the present invention is drug screening to identify modulators of an enzyme that catalyzes a biochemical reaction producing ADP or GDP, such as kinase, ATPase or GTPase. Thus, another aspect of the present invention relates to a method for selecting modulators of such an enzyme. Essentially, in this respect, the assay method described above can be performed both in the presence of one or more test compounds. If the activity of the enzyme is lower in the presence of the one or more test compounds than in the absence of compounds, then the compounds can be recognized as having an inhibitory activity against the enzyme. Of course, if the activity of the enzyme is higher in the presence of the one or more test compounds than in the absence of compounds, then the compounds can be recognized as a stimulator/activator activity against the enzyme.

Accordingly, the present invention provides a screening assay for selecting a modulator (inhibitor or activator) of the enzymatic activity of an enzyme that catalyzes a biochemical reaction producing ADP or GDP. The assay generally includes the steps of: (a) contacting a substrate with ATP or GTP in the presence of said enzyme as well as one or more test compounds, under conditions that would normally allow at least a portion of said ATP or GTP to be converted to ADP or GDP, respectively; (b) reacting the ADP or GDP with a phosphoryl group acceptor which is a hexose or hexose phosphate, in the presence of an ADP- or GDP-dependent hexokinase, a dehydrogenase, NAD(P) or an analog thereof, and a dye in an oxidized state, under conditions such that the dye in an oxidized state is converted to a reduced state with fluorescence emission; and (c) determining the activity of the enzyme based on the fluorescence emitted by the dye in the reduced state. Preferably, the dye is resazurin, and the dye in reduced state is resorufin. Also preferably, the reacting step is conducted in the presence of a divalent cation (e.g., $Mg^{2+}$, $Co^{2+}$, $Ca^{2+}$, $Zn^{2+}$, $Mn^{2+}$), and preferably at a concentration of at least 1 mM, more preferably at least 5 mM, and most preferably at 10 mM. Optionally, the steps of (a) (b) and (c) are conducted both in the presence of one or more test compounds and also, preferably in parallel, in the absence of the compounds. The measurements of the fluorescence emission from the dye in reduced state in both cases are compared.

In other words, as also will be apparent to a skilled artisan, the method of selecting modulators of the enzymes can be conducted similarly to the enzyme assay method described above, except that one or more test compounds are present with the enzyme, preferably in contact with the enzyme. That is, the enzyme assay is conducted in the presence of one or more test compounds, i.e., candidates of modulators of the enzyme. Preferably, a control assay is also done, in which the measuring is done in absence of any test compound. By comparing the enzyme activity measured in the presence and absence of a test compound, modulators of the enzyme can be selected.

As used herein, the term "selecting" or "select" compounds it is intended to encompass both (a) choosing compounds from a group previously unknown to be modulators of an enzyme activity; and (b) testing compounds that are known to be inhibitors or activators of an enzyme activity. Both types of compounds are generally referred to herein as "test compounds." The test compounds may include, by way of example, proteins (e.g., antibodies, small peptides, artificial or natural proteins), nucleic acids, and derivatives, mimetics and analogs thereof, and small organic molecules having a molecular weight of no greater than 10,000 daltons, more preferably less than 5,000 daltons. Preferably, the test compounds are provided in library formats known in the art, e.g., in chemically synthesized libraries, recombinantly expressed libraries (e.g., phage display libraries), and in vitro translation-based libraries (e.g., ribosome display libraries).

Peptidic test compounds may be peptides having L-amino acids and/or D-amino acids, phosphopeptides, and other types of peptides. The screened peptides can be of any size, but preferably have less than about 50 amino acids. Smaller peptides are easier to deliver into a patient's body. Various forms of modified peptides may also be screened. Like antibodies, peptides can also be provided in, e.g., combinatorial libraries. See generally, Gallop et al., *J. Med. Chem.*, 37:1233-1251 (1994). Methods for making random peptide libraries are disclosed in, e.g., Devlin et al., *Science*, 249: 404-406 (1990). Other suitable methods for constructing peptide libraries and screening peptides therefrom are disclosed in, e.g., Scott and Smith, *Science*, 249:386-390 (1990); Moran et al., *J. Am. Chem. Soc.*, 117:10787-10788 (1995) (a library of electronically tagged synthetic peptides); Stachelhaus et al., *Science*, 269:69-72 (1995); U.S. Pat. Nos. 6,156,511; 6,107,059; 6,015,561; 5,750,344; 5,834,318; 5,750,344, all of which are incorporated herein by reference. For example, random-sequence peptide phage display libraries may be generated by cloning synthetic oligonucleotides into the gene III or gene VIII of an *E. coli* filamentous phage. The thus generated phage can propagate in *E. coli*. and express peptides encoded by the oligonucleotides as fusion proteins on the surface of the phage. Scott and Smith, *Science*, 249:368-390 (1990). Alternatively, the "peptides on plasmids" method may also be used to form peptide libraries. In this method, random peptides may be fused to the C-terminus of the *E. coli*. Lac repressor by recombinant technologies and expressed from a plasmid that also contains Lac repressor-binding sites. As a result, the peptide fusions bind to the same plasmid that encodes them.

Small organic or inorganic non-peptide non-nucleotide compounds are preferred test compounds for the screening assays of the present invention. They too can be provided in a library format. See generally, Gordan et al. *J. Med. Chem.*, 37:1385-1401 (1994). For example, benzodiazepine libraries are provided in Bunin and Ellman, *J. Am. Chem. Soc.*, 114:10997-10998 (1992), which is incorporated herein by reference. Methods for constructing and screening peptoid libraries are disclosed in Simon et al., *Proc. Natl. Acad. Sci. USA*, 89:9367-9371 (1992). Methods for the biosynthesis of novel polyketides in a library format are described in McDaniel et al, *Science*, 262:1546-1550 (1993) and Kao et al., *Science*, 265:509-512 (1994). Various libraries of small organic molecules and methods of construction thereof are disclosed in U.S. Pat. Nos. 6,162,926 (multiply-substituted fullerene derivatives); 6,093,798 (hydroxamic acid derivatives); 5,962,337 (combinatorial 1,4-benzodiazepin-2,5-dione library); 5,877,278 (Synthesis of N-substituted oligomers); 5,866,341 (compositions and methods for screening drug libraries); 5,792,821 (polymerizable cyclodextrin derivatives); 5,766,963 (hydroxypropylamine library); and 5,698,685 (morpholino-subunit combinatorial library), all of which are incorporated herein by reference.

Other compounds such as oligonucleotides and peptide nucleic acids (PNA), and analogs and derivatives thereof may also be screened to identify clinically useful compounds. Combinatorial libraries of oligonucleotides are also known in the art. See Gold et al., *J. Biol. Chem.*, 270:13581-13584 (1995).

In yet another aspect of the present invention, a kit is provided for conveniently practicing the method or assay of the present invention. In one embodiment, the kit can include, preferably in a compartmentalized carrier, some or all of the following components: ATP or GTP; a phosphoryl group acceptor which is a hexose or hexose derivative such as hexose phosphate; an ADP- or GDP-dependent hexokinase; a dehydrogenase; NAD(P) or an analog thereof; a divalent cation-releasing salt; and a dye having an oxidized state and a reduced state, wherein the reduced state is associated with fluorescence emission whereas the oxidized state is substantially free of fluorescence emission. In a specific embodiment, the dye in oxidized state is resazurin or a salt or analog thereof, and optionally the kit further comprises diaphorase. In some embodiments, the kit further includes an enzyme that catalyzes a biochemical reaction producing ADP or GDP, such as kinase (protein kinase or non-protein kinase), ATPase or GTPase, and optionally a suitable substrate of the enzyme.

In preferred embodiments, the kit comprises, in a compartmentalized carrier: ATP; a phosphoryl group acceptor which is a hexose or hexose phosphate; an ADP-dependent hexokinase; a dehydrogenase; NAD(P) or an analog thereof; resazurin or a salt or analog thereof; and a divalent cation-releasing salt. Preferably, the phosphoryl group acceptor is D-glucose, the ADP-dependent hexokinase is ADP-dependent glucokinase described above, and the dehydrogenase is glucose-6-P dehydrogenase. Optionally, the kit further includes diaphorase. In specific embodiments, the kit further includes an enzyme that catalyzes a biochemical reaction producing ADP, such as kinase (protein kinase or non-protein kinase) and ATPase, and optionally a suitable substrate of the enzyme.

In one embodiment of the kit of the present invention, the kit includes (1) a reaction buffer comprising ATP, and optionally an ATPase or kinase, a divalent cation (e.g., $Mg^{2+}$, $Co^{2+}$, $Ca^{2+}$, $Zn^{2+}$, and $Mn^{2+}$), and optionally a suitable substrate of the ATPase or kinase, (2) a detection mixture comprising glucose, NAD(P), glucose-6-phosphate dehydrogenase, diaphorase, resazurin, and an ADP-dependent glucokinase.

The kit should contain, in a carrier or compartmentalized container, the above reagents. The carrier can be a container or support, in the form of, e.g., bag, box, tube, vial, rack, and is optionally compartmentalized. The carrier may define an enclosed confinement for safety purposes during shipment and storage.

As will be clear to skilled artisans, while the method illustrated in FIG. 1 is specific to kinases, the same principle can be readily adapted to ATPases. In addition, the applicability of the approach in FIG. 1 can be extended to the GTP-specific kinases and GTPases, provided that the *P. furiosus* GlkA protein, which is strictly ADP-specific, is replaced as the detection reagent with the ADP-dependent glucokinase/phosphofructokinse from *Methanococcus jannaschii* that is able to utilize both ADP and GDP as the donors of phosphate with comparable efficiencies.

EXAMPLES

Figure 2:
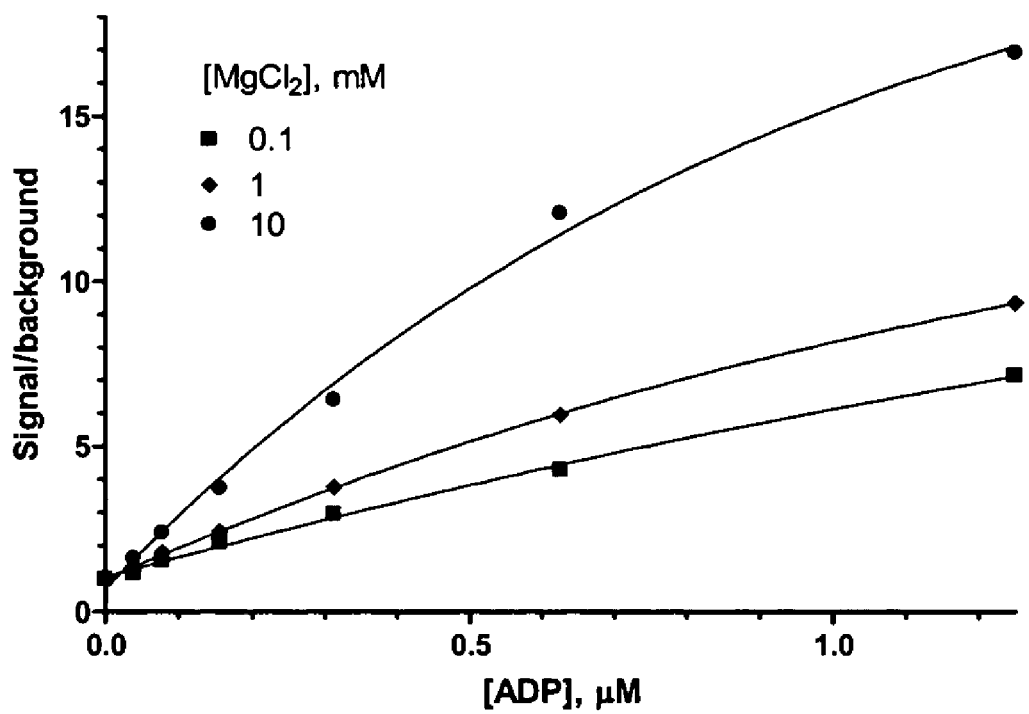
FIG. 2 illustrates the sensitivity and signal/background ratio of an assay for ADP in the presence of ATP at an excessive concentration.
Figure 4:
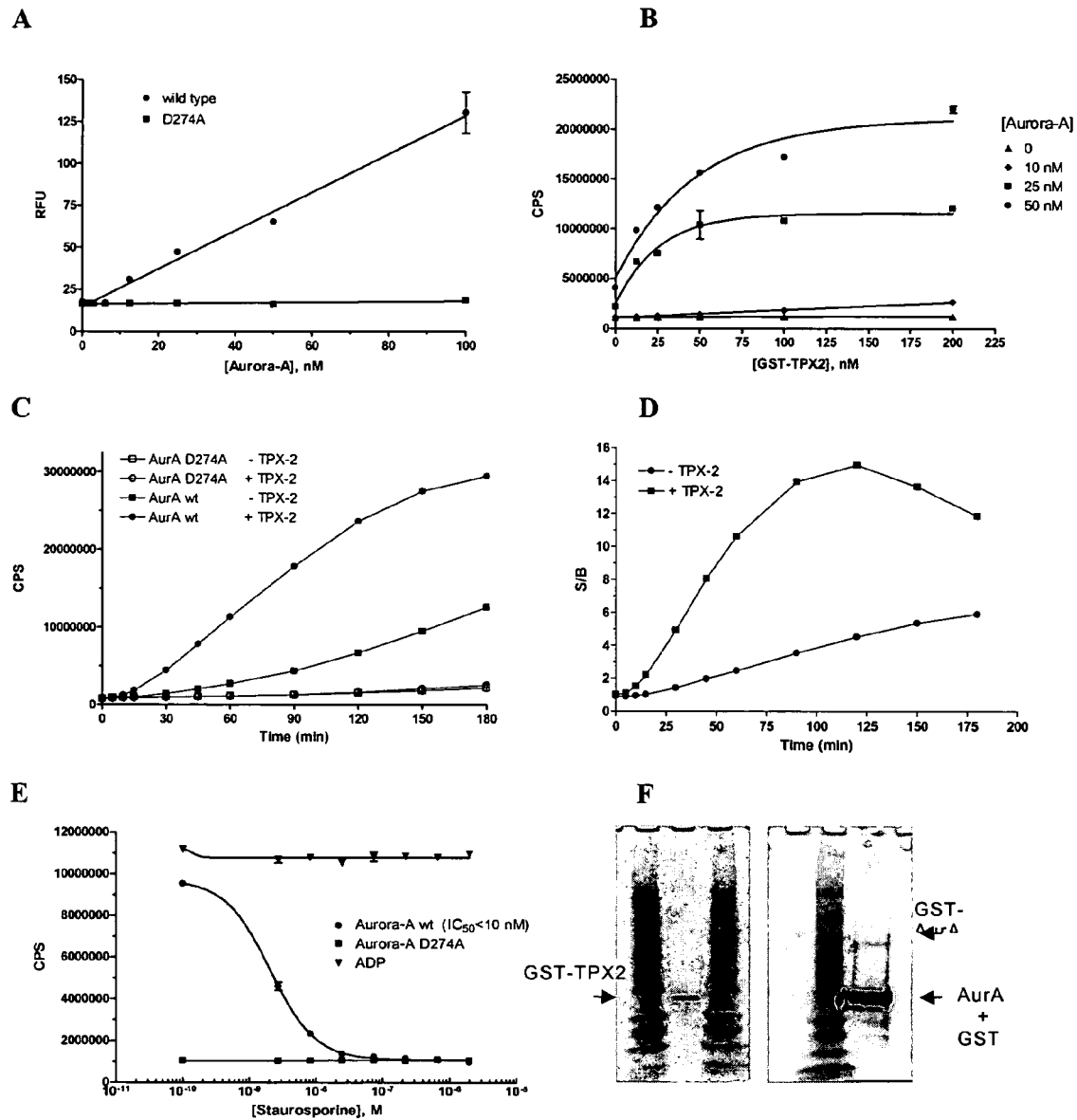
FIG. 4 shows the plots and results of a high throughput fluorometric assay for the TPX-2-stimulated protein kinase activity of Aurora-A.
Figure 5:
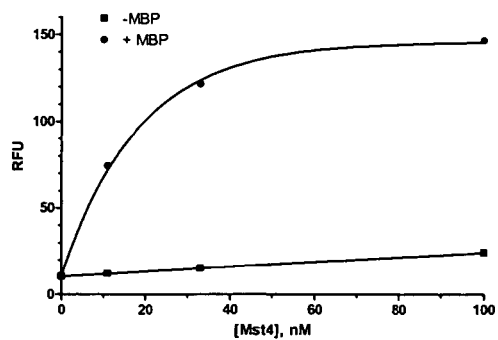
FIG. 5 shows the result of a high throughput assay for the Mst4 protein kinase activity.
Figure 5:
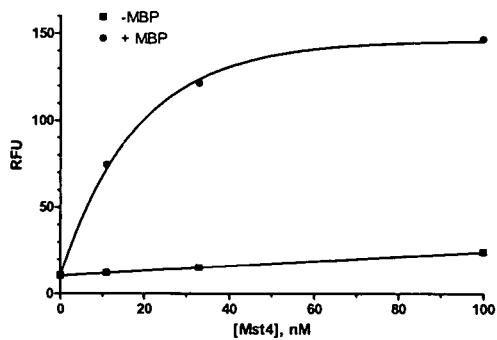
Figure 5:
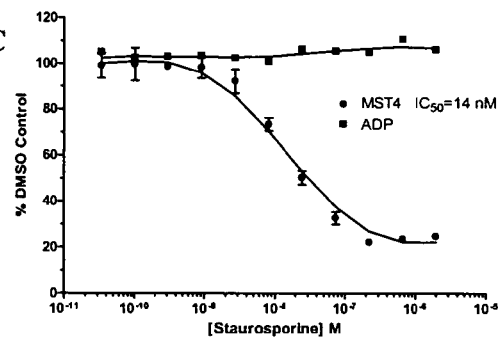
Figure 5:
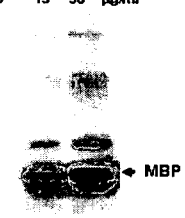
Figure 5:
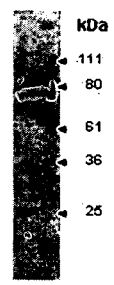
Figure 6:
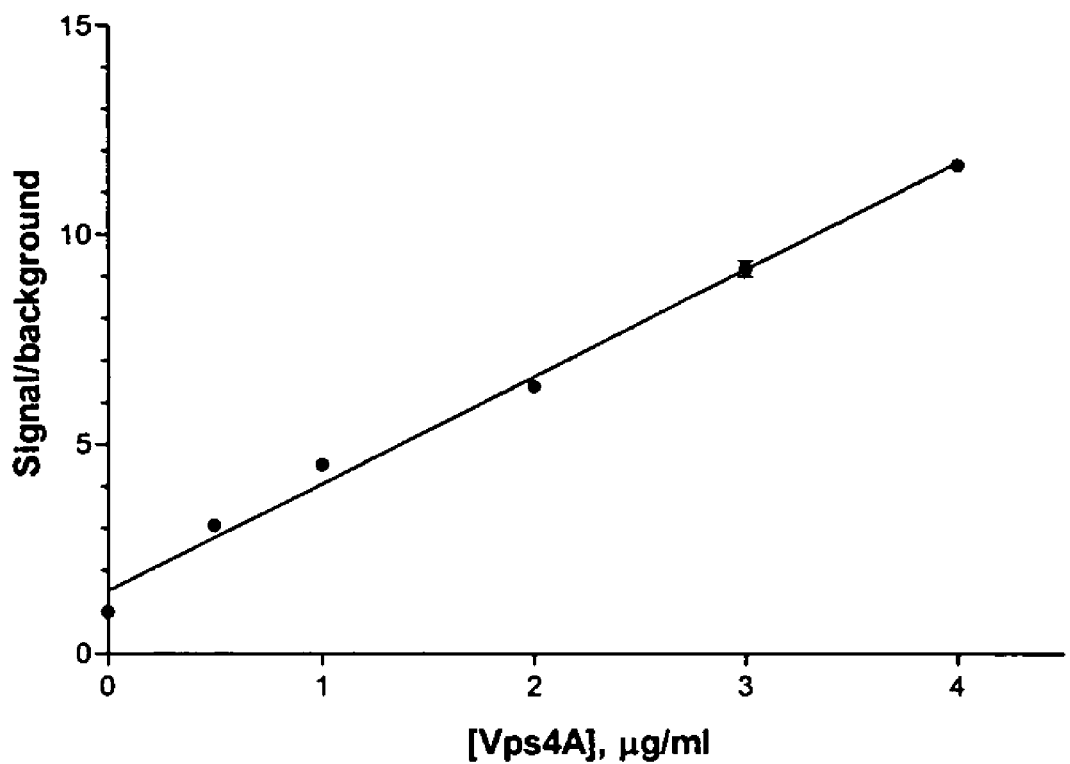
FIG. 6 shows the result of an assay for ATPase activity of Vps4Ap.

To date, we have demonstrated the utility and advantage of the proposed approach for the specific determination of ADP in the presence of ATP using the ADP-dependent glucokinase encoded by the GlkA gene from *Pyrococcus furiosus*. The lower limit of detection defined as the ADP concentration corresponding to signal-to-background ratio of two-fold was approximately 50 nM (FIG. 2). Utility of this technique for the determination of kinase activities has been demonstrated using several protein kinases, namely, casein kinase II (FIG. 3), Aurora-A (FIG. 4) and Mst4 (FIG. 5). Furthermore, it has been shown that the method can also be employed for monitoring activities of other ADP-generating enzymes such as, for instance, Vps4A ATPase (FIG. 6).

Example 1

Assay for ADP in the presence of ATP at excessive concentration. 100-ul aliquots of 50 mM Tris-HCl, pH 7.5, 5 μM ATP, 1 mM glucose, 20 μM NADP, 1 μM resazurin, 0.1 U/ml glucose-6-phosphate dehydrogenase, 0.02 U/ml diaphorase and 1 μg/ml GlkA were supplemented with ADP and magnesium chloride at indicated concentrations in FIG. 2 followed by incubation at room temperature for 15 min. Fluorescence intensities were determined using AnalystAD instrument ($\lambda$ex=420 nm; $\lambda$em=480 nm) and normalized to the values determined in the absence of ADP. The result is shown in FIG. 2.

Example 2

Figure 3:
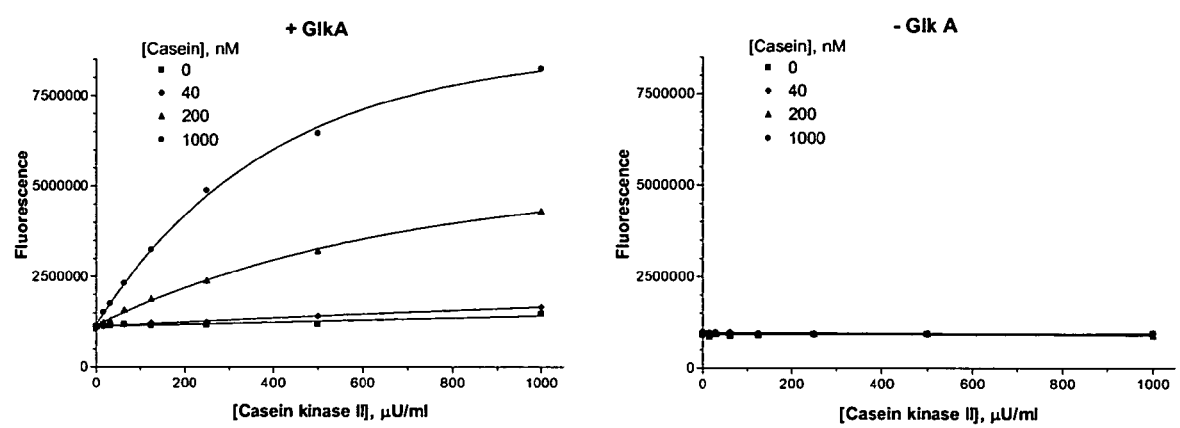
FIG. 3 shows an assay for the activity of casein kinase II.

Assay for the activity of casein kinase II. 90-μl aliquots of 50 mM Tris-HCl, pH 7.5 supplemented with 1 mM MgCl$_2$, 50 μM ATP (in-house purified) as well as casein and casein kinase II at increasing concentrations were incubated at room temperature for 1 hr. The 10-μl aliquots of 10× detection mix (10 mM glucose, 200 μM NADP, 2.5 μM resazurin, 1 U/ml glucose-6-phosphate dehydrogenase, 0.2 U/ml diaphorase) were added followed by incubation for 15 min in the presence (A) or in the absence (B) of GlkA at the concentration of 0.25 μg/ml. The fluorescence intensities were measured as described in Example 1. The result is shown in FIG. 3.

Example 3

High throughput fluorometric assay for the TPX2-stimulated protein kinase activity of Aurora-A. All the experiments were conducted using 50 mM Tris-HCl, pH 7.5, 5 μM ATP, 10 mM MgCl$_2$ as the assay buffer. The data shown on FIGS. 4A and 4B were generated using two-step assay procedure including Aurora-A-catalyzed kinase reaction followed by the assay of ADP produced. All other experiments were performed using single step assay format. A, comparative analysis of kinase activities of the wild type enzyme and D274A mutant protein performed in the absence of TPX-2. B, effects of GST-TPX2(1-50) on kinase activity. C, time course of signal development for the assays conducted using 25 nM kinase in the absence or in the presence of 50 nM GST-TPX2(1-50). The D274A mutant enzyme was used as negative control. D, time dependence of S/B ratio calculated using data shown on FIG. 4C. The background was defined as the fluorescence intensity of the samples supplemented with the mutant Aurora-A. E, inhibition of Aurora-A activity by staurosporine. The assays were performed using wild type or D274A mutant enzyme at 25 nM concentrations or 1.25 μM ADP. F, SDS-PAGE analysis of the recombinant GST-TPX2(1-50) and Aurora-A(101-403) (the latter protein was generated by cleavage of the GST fusion precursor with thrombin).

Example 4

High throughput assay for the Mst4 protein kinase activity. The result of the following are shown in FIGS. 5A-5E. A, correlation between signal intensity and concentration of target enzyme. The assay was performed in the absence or in the presence of 5 μM myelin basic protein using 50 mM Tris-HCl, pH 7.5, 5 μM ATP, 10 mM MgCl$_2$ supplemented with the ADP detection reagents as well as the wild type GST-MST4(1-317) at increasing concentrations. B, effect of K53M mutation on Mst4 kinase activity in the presence of 5 μM MBP. C, inhibition of Mst4 kinase by staurosporine. The assay was performed using 25 nM protein kinase. The combination of Mst4 and ATP was substituted with 1.25 μM ADP in control samples. D, $^{32}$P incorporation assay for Mst4 kinase activity towards MBP. E, SDS-PAGE analysis of GST-Mst4(1-317) purified from bacterial cells.

Example 5

Assay for ATPase activity of Vps4Ap. The 100-μl samples containing 50 mM Tris-HCl, pH 7.5, 100 μM ATP, 5 mM MgCl$_2$ as well as Vps4A protein at increasing concentrations were incubated at room temperature for 4 hours. 10-μl aliquots of 10× detection reagent (10 mM glucose, 100 μM NADP, 1 U/ml glucose-6-phosphate dehydrogenase, 0.2 U/ml diaphorase, 100 μM resazurin and 1 μg/ml GlkA) was added followed by the incubation at room temperature for 3 hours and measuring fluorescence intensities using Gemini XS instrument ($\lambda_{ex}$=510 nm, $\lambda_{em}$=590 nm). The result is shown in FIG. 6.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. A method for determining the activity of an ATPase or kinase that catalyzes a biochemical reaction producing ADP, comprising:

contacting a substrate with ATP in the presence of said ATPase or kinase under conditions such that at least a portion of said ATP is converted to ADP;

reacting the ADP with a phosphoryl group acceptor which is a hexose or hexose phosphate, in the presence of an ADP-dependent hexokinase, a dehydrogenase that oxidizes or dehydrogenates said hexose or hexose phosphate in the presence of, NAD(P) or an analog thereof, resazurin or a salt thereof, under conditions such that fluorescent resorufin is produced; and determining the activity of said ATPase or kinase based on measurement of fluorescence emitted by said resorufin.

2. The method of claim 1, wherein said hexose is D-glucose and said dehydrogenase is glucose-6-P dehydrogenase.

3. The method of claim 2, wherein said resazurin is converted to resorufin in the presence of diaphorase.

4. The method of claim 1, wherein the reacting step is conducted in the presence of a divalent cation.

5. The method of claim 1, wherein the reacting step is conducted in the presence of at least 1 mM of magnesium ion.

6. A method for determining the activity of an ATPase or kinase that catalyzes a biochemical reaction producing ADP, comprising:

contacting a substrate with ATP in the presence of said ATPase or kinase under conditions such that at least a portion of said ATP is converted to ADP wherein said contacting step is conducted in the presence of one or more test compounds to be tested for their ability to inhibit the ATPase or kinase;

reacting the ADP with a phosphoryl group acceptor which is a hexose or hexose phosphate, in the presence of an ADP-dependent hexokinase, a dehydrogenase that oxidizes or dehydrogenates said hexose or hexose phosphate in the presence of NAD(P) or an analog thereof, resazurin or a salt thereof, under conditions such that fluorescent resorufin is produced; and determining the activity of said ATPase or kinase based on measurement of fluorescence emitted by said resorufin.

7. A method for determining the activity of an ATPase or kinase that catalyzes a biochemical reaction producing ADP, comprising:

(a) contacting a substrate with ATP in the presence of said ATPase or kinase and under conditions such that at least a portion of said ATP is converted to ADP;

(b) reacting the ADP with D-glucose in the presence of an ADP-dependent glucokinase, a glucose-6-P dehydrogenase, NAD(P), resazurin, diaphorase and at least 1 mM of magnesium ion, under conditions such that fluorescent resorufin is produced;

(c) determining the activity of said ATPase or kinase based on measurement of fluorescence emitted by said resorufin;

(d) repeating the steps of (a) (b) and (c) in the presence of one or more test compounds; and (e) comparing the measurements of fluorescence in the presence and absence of said test compounds.

* * * * *